United States Patent [19]
Tehim et al.

[11] Patent Number: 5,824,676
[45] Date of Patent: Oct. 20, 1998

[54] 5-HT2 RECEPTOR LIGANDS

[75] Inventors: Ashok Tehim, Mississauga, Canada; Jian-min Fu, Elmsford, N.Y.; Sumanas Rakhit, Mississauga, Canada

[73] Assignee: Allelix Biopharmaceuticals Inc., Mississauga, Canada

[21] Appl. No.: 763,255

[22] Filed: Dec. 10, 1996

Related U.S. Application Data

[62] Division of Ser. No. 354,765, Dec. 12, 1994, Pat. No. 5,602,124.

[51] Int. Cl.$^6$ .................. A61K 31/55; C07D 403/04; C07D 417/04; C07D 413/04
[52] U.S. Cl. ............................................ 514/220; 540/547
[58] Field of Search ............................. 540/547; 514/220

[56] References Cited

U.S. PATENT DOCUMENTS

| | | | |
|---|---|---|---|
| 3,539,573 | 11/1970 | Schmutz | 260/268 |
| 3,546,226 | 12/1970 | Schmutz | 260/268 |
| 3,751,415 | 8/1973 | Schmutz | 260/268 |
| 3,758,479 | 9/1973 | Schmutz | 260/268 |
| 3,908,010 | 9/1975 | Schmutz | 424/250 |
| 3,983,234 | 9/1976 | Sayers | 424/250 |
| 4,096,261 | 6/1978 | Horrom | 424/250 |
| 4,115,574 | 9/1978 | Chakrabarti | 540/557 |
| 4,216,148 | 8/1980 | Hofman | 540/557 |
| 4,931,447 | 6/1990 | Foreman | 514/288 |
| 5,229,382 | 7/1993 | Chakrabarti | 540/557 |
| 5,354,747 | 10/1994 | Hansen | 514/211 |
| 5,602,121 | 2/1997 | Fu | 540/557 |

FOREIGN PATENT DOCUMENTS

| | | | |
|---|---|---|---|
| 772160 | 11/1967 | Canada | 260/239.11 |
| 1801523 | 6/1969 | Germany . | |
| 3134775 A1 | 3/1983 | Germany . | |
| 6609437 | 1/1967 | Netherlands . | |
| WO 9402462 | 2/1994 | WIPO . | |

OTHER PUBLICATIONS

Gianai et al Synthesis, 1985, p. 550 "A new facile synthesis of 11–oxo–10,11–dihydro–5H–dibenzo[b,e][1,4]diazepines".

Harris et al J Med Chem, 1982, 25:855 "Affinity of 10–(4–methylpiperazino)dibenz[b,f]oxepins for clozapine and spiroperidol binding sites in rat brain".

Klunder et al J Med Chem, 1992, 35:1887 "Novel non-nucleoside inhibitors of HIV–1 reverse transcriptase. tricyclic pyridobenzoxazepinones and dibenzoxazepinones".

de Paulis et al J Med Chem, 1981, 24(9):1021 "Synthesis of clozapine analogues and their affinity for clozapine and spiroperidol binding sites in rat brain".

Sindelar et al Coll. Czechoslov. Chem. Commun., 1977, 42:2231 Noncataleptic potential neuroleptics: 2–nitro and 2–hydroxy derivatives of 10–(4–methylpiperzino)–10, 11–dihydrodibenzo[b,f]thiepin.

The Merck Manual of Diagnosis and Thrapy, 15th ed. (1987), Berkow, M.D. editor, pp. 2486–2487.

Chakrabarti et al., *J. Med Chem.*, "Effects of Conformationally Restricted 4–Piperazinyl–10H–thienobenzodiazepine Neuroleptics on Central Dopaminergic and Cholinergic Systems", 25, 1133–1140 (1982).

Šindelář et al., *Coll. Czechoslov. Chem. Commun.*, "Neuroleptics of the 10–Piperazino–10,11–Dihydrobidenzo[b,f] Thiepin Series and Related Substances: Piperazine–Alkylated Homologues of Octoclothepin and Methiothepin; 5,5–Dimethyl–10,11–Dihydro–5H–Dibenzo[b,f]Silepin Analogue of Perathiepin", 41, 910–922 (1976).

Steiner et al., *J. Med. Chem.*, "Tricyclic Epines. Novel (E)–and (Z)–11H–Dibenz[b,e]azepines as Potential Central Nervous System Agents. Variation of the Basic Side Chain", 29, 1877–1888 (1986).

*Primary Examiner*—Mark L. Berch
*Attorney, Agent, or Firm*—Nikaido Marmelstein Murray & Oram LLP

[57] ABSTRACT

Described herein are 5-HT2 receptor-selective compounds of Formula I:

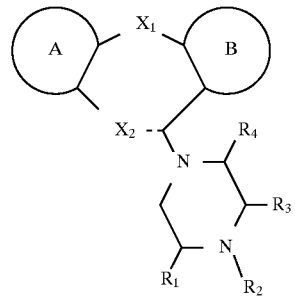

wherein:
A and B are independently selected, optionally substituted, saturated or unsaturated 5- or 6-membered, homo- or heterocyclic rings;

$X_1$ is selected from $CH_2$, O, NH, S, C=O, CH—OH, CH—N($C_{1-4}$alkyl)$_2$, C=CHCl, C=CHCN, N—$C_{1-4}$alkyl, N-acetyl, $SO_2$ and SO;

$X_2$—is selected from N=, $CH_2$—, CH=, C(O)—, O—, and S—;

$R_1$ is $C_{1-6}$alkyl optionally substituted with a substituent selected from OH, halo, $C_{1-4}$alkyl and $C_{1-4}$alkoxy; and $R_2$, $R_3$ and $R_4$ are independently selected from H and $R_1$; and acid addition salts, solvates and hydrates thereof. Their use as ligands for serotonin 5-HT2 receptor identification and in a drug screening program, and as pharmaceuticals to treat indications in which the 5-HT2 receptor is implicated, such as hypertension, thrombosis, migraine, vasospasm, ischemia, depression, anxiety, schizophrenia, sleep disorders and appetite disorders is also described.

17 Claims, No Drawings

5-HT2 RECEPTOR LIGANDS

This is a division of application Ser. No. 08/354,765 filed Dec. 12, 1994, U.S. Pat. No. 5,602,124.

This invention relates to compounds that bind selectively to the serotonin receptor b 5-HT2, to the preparation of such compounds and to the use of such compounds for therapeutic and drug screening purposes.

BACKGROUND TO THE INVENTION

Neuronal and peripheral cell receptors that bind the neurotransmitter serotonin constitute a group of at least seven structurally distinct proteins that can now be produced using recombinant-DNA techniques. These techniques have been applied to construct cell lines that incorporate the serotonin receptor in their membranes, to provide a valuable, regenerable and homogeneous source of substrate with which chemical libraries can be screened to identify potential CNS-active drugs.

Recent evidence strongly implicates the serotonin receptor classified as 5-HT2 in the etiology of such medical conditions as hypertension, thrombosis, migraine, vasospasm, ischemia, depression, anxiety, schizophrenia, sleep disorders and appetite disorders. It has been suggested that compounds capable of interfering with the function of this receptor, particularly when there is an excess of circulating serotonin, would be useful to treat these conditions (see U.S. Pat. No. 4,931,447 and WO 94/02462). However, the tendency for ligands to bind indiscriminately to various types of dopamine receptors, such as the dopamine D4 and D2 receptors, has made difficult the development of drugs that are 5-HT2 receptor-selective. It would nevertheless be desirable to provide such a compound, particularly so that side effects are minimized during treatment of the conditions noted above.

It is an object of the present invention to provide a compound having an improved 5-HT2 receptor selectivity profile.

It is a further object of the present invention to provide a pharmaceutical composition comprising a compound of the present invention, as active ingredient.

SUMMARY OF THE INVENTION

According to one aspect of the present invention, there is provided a compound of Formula I:

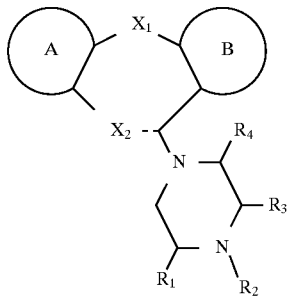

wherein:

A and B are independently selected, optionally substituted, saturated or unsaturated 5- or 6-membered, homo- or heterocyclic rings;

$X_1$ is selected from $CH_2$, O, NH, S, C=O, CH—OH, CH—N($C_{1-4}$alkyl)$_2$, C=CHCl, C=CHCN, N-$C_{1-4}$alkyl, N-acetyl, $SO_2$ and SO;

$X_2$—is selected from N=, $CH_2$—, CH=, C(O)—, O—, and S—;

$R_1$ is $C_{1-6}$alkyl optionally substituted with a substituent selected from OH, halo, $C_{1-4}$alkyl and $C_{1-4}$alkoxy; and $R_2$, $R_3$ and $R_4$ are independently selected from H and $R_1$; and acid addition salts, solvates and hydrates thereof.

According to another aspect of the invention, there is provided a pharmaceutical composition comprising a compound of Formula I and a pharmaceutically acceptable carrier.

In a further aspect of the invention, there is provided an analytical method in which a compound of the invention is used either to distinguish the 5-HT2 receptor from dopamine receptors such as the D2 and D4 sub-types.

These and other aspects of the present invention are now described in greater detail hereinbelow.

DETAILED DESCRIPTION AND PREFERRED EMBODIMENTS

The invention relates to compounds that bind the serotonin 5-HT2 receptor in a selective manner, relative to dopamine D2 and D4 receptors. In accordance with one of its aspects, the present invention accordingly provides compounds that conform to Formula I:

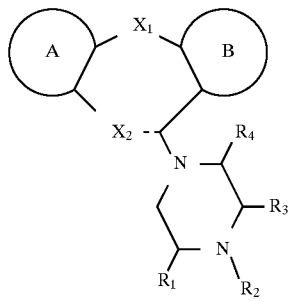

In embodiments of the invention, $R_1$ is linear or branched $C_{1-6}$alkyl optionally substituted with a substituent selected from OH, halo, $C_{1-4}$alkyl and $C_{1-4}$alkoxy. Particular embodiments of the invention include those in which $R_1$ is $C_{1-6}$alkyl such as methyl, ethyl, linear or branched propyl, butyl, pentyl and hexyl. More particularly $R_1$ is methyl or ethyl and specifically $R_1$ is methyl.

In embodiments of the invention, $R_2$, $R_3$ and $R_4$ are independently selected from H and $R_1$. Particular embodiments of the invention include those in which $R_2$, $R_3$ and $R_4$ are independently selected from H and $C_{1-6}$alkyl. Other particular embodiments of the invention include those in which $R_2$, $R_3$ and $R_4$ are independently H, methyl or ethyl. In specific embodiments $R_2$ is H and $R_3$ and $R_4$ are independently H or methyl. In other specific embodiments $R_3$ is methyl and $R_4$ is H.

In specific embodiments of the invention, the piperazine ring coupled to the tricyclic structure is selected from 3,6-dimethylpiperazine and 2,6-dimethyl piperazine.

The tricyclic function to which the derivatized piperazine is coupled can have various structures and will typically incorporate those found to be important for serotonin 5-HT2 receptor binding. In other words, the tricycles suitable for coupling the derivatized piperazine are those which, when substituted by functions other than the derivatized piperazine, are determined by the assay herein described, to bind the 5-HT2 receptor (preferably the human 5-HT2 receptor) with an affinity not greater than 1 µM (Ki). In particular, the rings A and B are selected, according to embodiments of the invention, from benzene, pyridine, pyrimidine, pyrazine, pyridazine, pyrole, imidazole, triazole, pyrazole, thiophene, thiazole, furan and pyran. In a particular embodiment, ring A is selected from benzene and pyridine and ring B is selected from benzene, pyridine, pyrimidine, pyrazine, pyridazine, pyrole, imidazole, triazole, pyrazole, thiophene, thiazole, furan and pyran; and is particularly selected from benzene and pyridine. In specific embodiments of the invention, both rings A and B are benzene. It is to be appreciated that when rings A and B are heterocycles, the heteroatoms are shared with the central seven membered ring only when the shared heteroatom is N. Such tricycles are within the scope of the Formula I; one embodiment of which is described by Lednicer et al in *The Organic Chemistry of Drug Synthesis*, (1992, John Wiley & Sons Inc., New York) wherein ring B is imidazole that is fused to a thiazepine at one of the imidazole nitrogen atoms.

One or both rings A and B may be substituted with from 1 to 3, usually 1 or 2, substituents. When substituted, the substituents are selected from hydroxyl, halo, $C_{1-4}$alkyl, amino, nitro, cyano, halo-substituted $C_{1-4}$alkyl, $C_{1-4}$alkoxy, halo-substituted $C_{1-4}$alkoxy, $C_{1-4}$alkoxycarbonyl, $C_{1-4}$acyl, halo-substituted $C_{1-4}$acyl, cyclo-$C_{3-7}$alkyl, thio-$C_{1-4}$alkylene, $C_{1-4}$alkylthio, halo-substituted $C_{1-4}$alkylthio, cyanothio, tetrazolyl, N- piperidinyl, N-piperazinyl, N-morpholinyl, acetamido, $C_{1-4}$alkylsulfonyl, halosulfonyl, halo-substituted $C_{1-4}$alkylsulfonyl, $C_{1-4}$alkylsulfoxyl, sulfonamido, $C_{1-4}$alkylseleno, and $OSO_3H$.

Substitution sites on rings A and B will be limited in practice to the carbon atoms on the ring that are not shared with the central seven membered ring. For example, a benzene ring can accomodate up to 4 substituents; pyridine, and pyran, rings can accomodate up to 3 substituents; pyrimidine, pyrazine, pyridazine, pyrole, furan and thiophene rings can accomodate up to 2 substituents; imidazole, pyrazole and thiazole rings can accomodate only 1 substituent; and a triazole ring can accomodate no substituents. It is also to be understood that rings A and B may incorporate substituents at nitrogen atoms on the ring that are not shared with the central seven membered ring. For example the NH member of an imidazole ring may be substituted. In particular embodiments, rings A and B are substituted with from 1 to 2 substituents selected from chloro, fluoro, methyl, trifluoromethyl, methoxy, nitro, cyano and methylthio. In particularly preferred embodiments ring A is benzene substituted with 1 or 2 substituents selected from chloro, methyl, nitro and cyano and ring B is benzene substituted with 1 or 2 substituents selected from chloro, methoxy, trifluoromethyl and nitro.

In the central, 7-membered ring of the tricycle, $X_1$ may be any one of $CH_2$, O, NH, S, C=O, CH—OH, CH—N($C_{1-4}$alkyl)$_2$, C=CHCl, C=CHCN, N—$C_{1-4}$alkyl, N-acetyl, $SO_2$ and SO, while $X_2$—may be any one of N=, $CH_2$—, CH=, C(O)—, O—, and S—. In a particular embodiment of the invention, $X_1$ is O, S or NH. In another embodiment, $X_2$—is N= or CH=. In a particularly preferred embodiment, $X_1$ is O, S or NH and $X_2$—is N= or CH=. In specific embodiments $X_1$ and $X_2$—are selected to form a seven membered ring selected from oxazepine, diazepine, thiazepine and thiepine.

In preferred embodiments $X_1$ and $X_2$—together with rings A and B are selected to form a tricycle that is selected from 5H-dibenzo[b,e][1,4]diazepine that is optionally substituted, for example with one of 7,8-dichloro, 7,8-dimethyl, 2-chloro, 3-chloro, 4-chloro, 2,4-dichloro, 4,7,8-trichloro, 2-trifluoromethyl, 1-fluoro, or 2-methoxy; dibenz[b,f][1,4]oxazepine that is optionally substituted, for example with one of 4-nitro, 8-chloro, 4-cyano or 4-chloro; dibenzo[b,f]thiepine that is optionally substituted, for example with one of 2-nitro or 2-chloro; 11H-dibenzo[b,f]thiepine that is optionally substituted, for example with 2-methylthio; and dibenzo[b,f][1,4]thiazepine that is optionally substituted, for example with 8-chloro. In a specific embodiment of the invention, $X_1$ and $X_2$—together with rings A and B are form a tricycle which is 8-chlorodibenz[b,f][1,4]oxazepine.

In a particular embodiment of the invention, there are provided compounds of formula (I) that bind to the 5-HT2 receptor in a selective manner relative to the dopamine D2 and D4 receptors, including:

8-chloro-11-(3,5-dimethyl-1-piperazinyl)-dibenz[b,f][1,4]oxazepine;

11-(3,5-dimethyl-1-piperazinyl)-dibenz[b,f] [1,4]oxazepine;

3-chloro-11-(3,5-dimethyl-1-piperazinyl)-5H-dibenzo[b,e][1,4]diazepine; and 11-(2,5-dimethyl-1-piperazinyl)-dibenz[b,f][1,4]oxazepine.

In a more preferred embodiment, there are provided compounds of formula (I) that bind to the 5-HT2 receptor in a selective manner relative to the dopamine D2 and D4 receptors, including:

8-chloro-11-(3,5-dimethyl-1-piperazinyl)-dibenz[b,f][1,4]oxazepine; and 3-chloro-11-(3,5-dimethyl-1-piperazinyl)-5H-dibenz[b,e][1,4]diazepine.

In a more preferred embodiment, there are provided compounds of formula (I) that bind to the 5-HT2 receptor in a selective manner relative to the dopamine D2 and D4 receptors, including:

11-(2,5-dimethyl-1-piperazinyl)-dibenz[b,f][1,4]oxazepine.

Acid addition salts of the compound of Formula I include for example those formed with inorganic acids e.g. hydrochloric, sulphuric or phosphoric acids and organic acids e.g. succinic, maleic, acetic or fumaric acid. Other non-pharmaceutically acceptable salts e.g. oxalates may be used for example in the isolation of compounds of Formula I for ligand use, or for subsequent conversion to a pharmaceutically acceptable acid addition salt. Also included within the scope of the invention are solvates and hydrates of the invention.

The conversion of a given compound salt to a desired compound salt is achieved by applying standard techniques, in which an aqueous solution of the given salt is treated with a solution of base e.g. sodium carbonate or potassium hydroxide, to liberate the free base which is then extracted into an appropriate solvent, such as ether. The free base is then separated from the aqueous portion, dried, and treated with the requisite acid to give the desired salt.

It will be appreciated that certain compounds of Formula I may contain an asymmetric centre. Such compounds will exist as two (or more) optical isomers (enantiomers). Both the pure enantiomers and the racemic mixtures (50% of each enantiomer), as well as unequal mixtures of the two, are included within the scope of the present invention. Further, all diastereomeric forms possible (pure enantiomers and mixtures thereof) are within the scope of the invention.

The compounds of the present invention can be prepared by processes analogous to those known in the art. The present invention therefore provides, in a further aspect, a process for the preparation of a compound of Formula I or a salt, solvate or hydrate thereof, which comprises the step of coupling a reagent of Formula A:

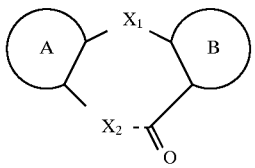

with a reagent of Formula B:

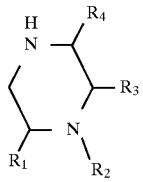

using a Lewis acid such as $TiCl_4$ or $BF_3 \cdot Et_2O$.

Reagent (A) can be obtained commercially or can be synthesized using established ring closure procedures. For example, when $X_1$ is NH and $X_2$—is N= (a diazepine), reagent (A) may be prepared according to the procedures described by Giani et al (Synthesis, 1985, 550) by refluxing equimolar amounts of 2-chlorobenzoic acid, o-phenylene-diamine and powdered copper in chlorobenzene. The following is a schematic representation of the reaction to obtain the diazepine form of reagent (A):

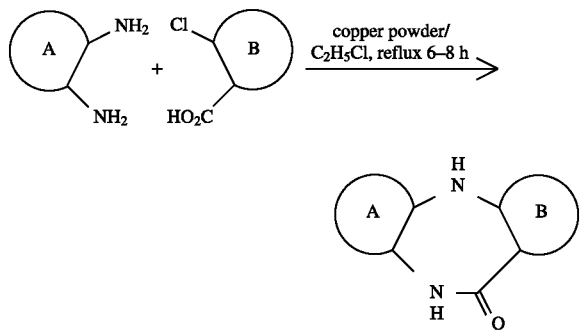

When $X_1$ is O and $X_2$—is N= (an oxazepine), reagent (A) may be prepared according to the procedures described by Klunder (J. Med. Chem. 1992, 35:1887) by condensation of a 2-aminophenol with 2-chloro-5-nitrobenzoyl chloride in THF to afford the corresponding carboxamide followed by refluxing with NaOH for ring closure. The following is a schematic representation of the steps to obtain the oxazepine form of reagent (A):

The thiepine form of reagent (A), i.e. when $X_1$ is S and $X_2$—is CH=, may be prepared according to the procedures described by Sindelar et al (Collect. Czech. Chem. Commun, 1983, 48(4):1187). When reagent (A) is an oxepine i.e. when $X_1$ is O and $X_2$—is $CH_2$—, it may be prepared in the manner reported by Harris et al (J. Med. Chem., 1982, 25(7):855); and the corresponding cycloheptene reagent (A) i.e. when $X_1$ and $X_2$—are both $CH_2$, may be prepared as reported by De Paulis et al (J. Med. Chem. 1981, 24(9): 1021). The thiazepine reagent (A) may be prepared in a four step process starting from 1-bromo-2-nitrobenzene and methyl thiosalicylate. The steps involve coupling; reduction of the nitro group; hydrolysis of the ester group; and finally ring closure.

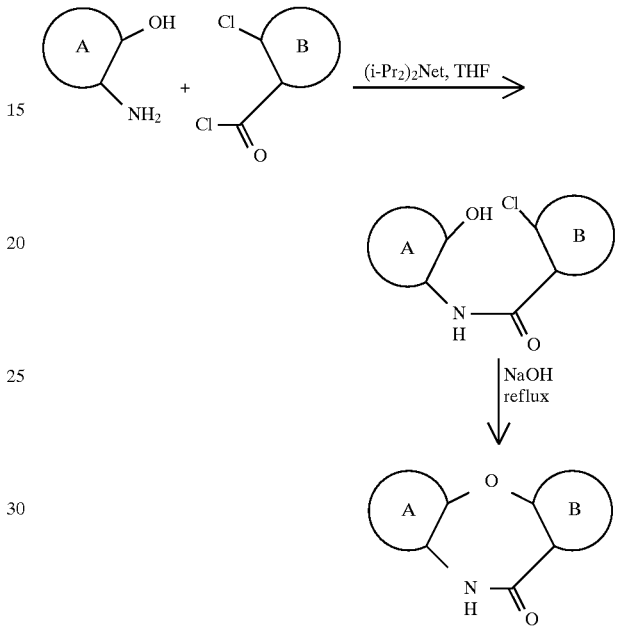

Reagents of Formula B are commercially available or else can be synthesized using established synthetic techniques from starting materials that are commercially available.

For use as a ligand, the present compounds can be stored in packaged form for reconstitution and use. The compounds can be used to distinguish 5-HT2 receptors from other receptor types, for example dopamine, glutamate and opioid receptors, within a population of receptors and in particular to distinguish from the dopamine D4 and D2 receptors. The latter can be achieved by incubating preparations of the 5-HT2 receptor and of the D4 and/or D2 receptor with a 5-HT2 selective compound of the invention and then incubating the resulting preparation with a radiolabelled serotonin receptor ligand, such as $^3$H-ketanserin. The 5-HT2 and dopamine receptors are then distinguished by determining the difference in membrane-bound radioactivity, with the 5-HT2 receptor exhibiting lesser radioactivity, i.e., lesser $^3$H-ketanserin binding.

In another embodiment of the invention, the compound is provided in labelled form, such as radiolabelled form e.g. labelled by incorporation within its structure of $^3$H or $^{14}$C or by conjugation to $^{125}$I. Such radiolabelled forms can be used to directly to distinguish between 5-HT2 and dopamine D4 and D2 receptors. Furthermore, radiolabelled forms of the present compounds can be exploited to screen for more potent serotonin 5-HT2 ligands, by determining the ability of the test ligand to displace the radiolabelled compound of the present invention.

The binding profile of the present compounds indicates their utility as pharmaceuticals that may be useful for the treatment of various conditions in which the use of a serotonin 5-HT2 receptor ligand is indicated, such as for the treatment of anxiety and schizophrenia.

For use in medicine, the compounds of the present invention are usually administered in a standard pharmaceutical composition. The present invention therefore provides, in a further aspect, pharmaceutical compositions comprising an effective amount of a compound of Formula I or a pharmaceutically acceptable salt, solvate or hydrate thereof and a pharmaceutically acceptable carrier.

The compounds of the present invention may be administered by an convenient route, for example by oral, parenteral, buccal, sublingual, nasal, rectal or transdermal administration and the pharmaceutical compositions formulated accordingly.

The compounds and their pharmaceutically acceptable salts which are active when given orally can be formulated as liquids, for example syrups, suspensions or emulsions, tablets, capsules and lozenges.

A liquid formulation will generally consist of a suspension or solution of the compound or pharmaceutically acceptable salt in a suitable pharmaceutical liquid carrier for example, ethanol, glycerine, non-aqueous solvent, for example polyethylene glycol, oils, or water with a suspending agent, preservative, flavouring or colouring agent.

A composition in the form of a tablet can be prepared using any suitable pharmaceutical carrier routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into hard gelatin capsule; alternatively, a dispersion or suspension can be prepared using any suitable pharmaceutical carrier, for example aqueous gums, celluloses, silicates or oils and the dispersion or suspension filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilized and then reconstituted with a suitable solvent just prior to administration.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as flurochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine.

Compositions for rectal administration are conveniently in the form of suppositories containing a conventional suppository base such as cocoa butter.

Preferably, the composition is in unit dose form such as a tablet, capsule or ampoule. Suitable unit doses i.e. therapeutically effective amounts; can be determined during clinical trials designed appropriately for each of the conditions for which administration of a chosen compound is indicated and will of course vary depending on the desired clinical endpoint. It is anticipated that dosage sizes appropriate for administering the compounds of the examples will be in the range from about 0.1 to about 500 mg/kg body weight eg. 0.1 to about 100 mg/kg body weight, and will be administered in a frequency appropriate for initial and maintenance treatments.

EXAMPLE 1

11-(3,5-dimethyl-1-piperazinyl)-dibenz[b,f][1,4] oxazepine

To a stirred solution of 10,11-dihydro-dibenz[b,f][1,4]oxazepin-11-one (0.4 g; 1.9 mmol; Aldrich) in dry toluene (20 mL) at room temperature was added 2,6-dimethyl piperazine (0.99 g; 8.7 mmol; Aldrich) followed by the dropwise addition of $TiCl_4$ (1M in toluene, 2.27 mL; 2.27 mmol). The reaction mixture was refluxed for 2 hours, cooled to room temperature and then poured into an ammonium hydroxide solution (30%, 50 mL). The resulting mixture was extracted with dichloromethane (4×75 mL), and the combined organic phases were then dried ($K_2CO_3$) and concentrated. Purification of the product was conducted on silica gel using $CHCl_3$:MeOH (94:6) eluant to give 0.353 g (60%) of 11-(3,5-dimethyl-1-piperazinyl)-dibenz[b,f][1,4]oxazepine as a pale yellow solid; m.p. 112°–114° C.

EXAMPLE 2

8-chloro-11-(3,5-dimethyl-1-piperazinyl)-dibenz[b,f][1,4]oxazepine

The compound 8-chloro-11-(3,5-dimethyl-1-piperazinyl)-dibenz[b,f][1,4]oxazepine was produced in the manner described in example 1, but using the 8-chloro analog of 10,11-dibenz[b,f][1,4]oxazepin-11-one as starting material, for reaction with 2,6-dimethyl piperazine. The 8-chloro compound was produced according to the protocol reported by Coyne et al, in J. Med. Chem., 1967, 10:541. Briefly, this entailed coupling potassium salicylaldehyde with 2,5-dichloronitrobenzene, followed by oxidation to the carboxylic acid, reduction of nitro, and finally ring closure, to yield the desired 8-chloro starting material (m.p. 256°–258° C). The 8-chloro starting material was then reacted with 2,6-dimethyl piperazine in the manner described in example 1, and 8-chloro-11-(3,5-dimethyl-1-piperazinyl)-dibenz[b,f][1,4]oxazepine was obtained as a pale yellow solid (51%); m.p. 154°–56° C.

EXAMPLE 3

11-(2,5-dimethyl-1-piperazinyl)-dibenz[b,f][1,4] oxazepine 10,11-dibenz[b,f][1,4]oxazepin-11-one (Aldrich) was reacted with 2,5-dimethyl piperazine (Aldrich) in the manner described in example 1, to give 11-(2,5-dimethyl-1- piperazinyl)-dibenz[b,f][1,4]oxazepine as a yellow solid (21%); m.p. 46°–48° C.

EXAMPLE 4

3-chloro-11-(3,5-dimethyl-1-piperazinyl)-5H-dibenz [b,e] [1,4]diazepine

The starting material, 3-chloro-10,11-dihydro-5H-dibenz [b,e][1,4]diazepin-11-one was produced according to the protocol reported by Giani et al, in Synthesis, 1985, 550. The 3-chloro lactam was then reacted with 2,6-dimethyl piperazine in the manner described in example 1, and 3-chloro-11-(3,5-dimethyl-1-piperazinyl)-5H-dibenz[b,e][1,4] diazepine was obtained as a brown solid (55%); m.p. 132°–34° C.

EXAMPLE 5

5-HT2 Receptor Binding Assay

5-HT2 receptor-binding affinities of the compounds of examples 1–4 were evaluated according to their ability to reduce binding of tritiated ketanserin, a serotonin receptor antagonist. The potency of the test compound to reduce $^3$H-ketanserin binding is directly correlated to its binding affinity for the receptor.

5-HT2 Receptor Preparation

Rat frontal cortex tissue was initially prepared by Analytical Biological Services by the following steps: homogenizing in 10 volumes of 0.32M sucrose at 4° C.; centrifuging at 900×g for 10 minutes; centrifuging supernatant at 48,000×g for 20 minutes; suspending pellet in 20 volumes 50 mM Tris HCl, pH 7.7 containing 5 mM calcium chloride; incubating at 37° C. for 30 minutes; centrifuging at 48,000×g for 30 minutes; suspending pellets in 2 volumes of buffer and storing in 15 mL aliquots at −70° C. On day of study, tissues were thawed on ice for 20 minutes. The entire pellet was resuspended in 5 mL of buffer (50 mM Tris, 0.5 mM EDTA, 10 mM MgSO$_4$, 10 $\mu$M pargyline, 0.1% ascorbic acid, pH 7.4) at 4° C. and sonicated with a Sonifier Cell Disrupter 350 at 8 microtip units for 6 seconds power 80. The protein concentration was determined using the Pierce BCA Assay, adding 1 $\mu$L of membrane preparation per sample, in triplicate. Membrane preparations were made in incubation buffer.

Total $^3$H-ketanserin Binding

The incubation was started in 12×75 mm polypropylene glass tubes by the addition of 400 $\mu$L membrane preparation (100 $\mu$g protein) to a solution of 500 $\mu$L incubation buffer (50 mM Tris, 0.5 mM EDTA, 10 mM MgSO$_4$, 10 $\mu$M pargyline, 0.1% ascorbic acid, pH 7.4) and 100 $\mu$L $^3$H-ketanserin (1 nM final concentration, 85 Ci/mmol, NEN Research Products). The tubes were vortexed and incubated at room temperature for 30 minutes. The binding reaction was stopped by filtering. The samples were filtered under vacuum over glass fibre filters (Whatman GF/B) soaked in 0.3% polyethylenimine (PEI) in 50 mM Tris (pH 7.4) for 2 hours and then washed 3 times with 5 mL ice cold 50 mM Tris -buffer (pH 7.4) using a Brandell Cell Harvester. Individual filter disks were put in scintilation vials (Biovials, Beckman). Ready Protein Plus liquid scintilant (5 mL, from Beckman) was added and the vials were counted by liquid scintillation spectrophotometry (Beckman LSC 6500) after equilibrating for three hours at room temperature to give total bidning ($B_T$).

Non-Specific Binding

The incubation was started in 12×75 mm polypropylene tubes by the addition of 400 $\mu$L membrane preparation (100 $\mu$g protein) to a solution of 500 $\mu$L methysergide (30 $\mu$M final conc. from 1 mM stock dissolved in DMS0 and diluted in incubation buffer, Research Biochemicals Inc.) and 100 $\mu$L $^3$H-ketanserin (1 nM final concentration, 85 Ci/mmol, NEN Research Products). The tubes were vortexed and incubated at room temperature for 30 minutes. The binding reaction was stopped by filtering. The filters were washed and counted using the same procedure as in the total binding assay described above to give the non-specific binding value (NSB).

Displacement Binding

The incubation was started in 12×75 mm polypropylene tubes by the addition of 400 $\mu$L membrane preparation (100 $\mu$g protein) to a solution of 500 $\mu$L test compound (initially 1 and 0.1M final conc. in incubation buffer) and 100 $\mu$L $^3$H-ketanserin (1 nM final concentration, 85 Ci/mmol, NEN Research Products). The tubes were vortexed and incubated at room temperature for 30 minutes. The binding reaction was stopped by filtering. The filters were washed and counted using the same procedure as in the total binding assay described above to give the displacement binding value ($B_D$).

Calculations

The test compounds were initially assayed at 1 and 0.1 $\mu$M and then at a range of 30 concentrations chosen such that the middle dose would cause about 50% inhibition of $^3$H-ketanserin binding. Specific binding in the absence of test compound ($B_O$) was the difference of total binding ($B_T$) minus non-specific binding (NSB) and similarly specific binding (in the presence of test compound) (B) was the difference of displacement binding ($B_D$) minus non-specific binding (NSB). IC$_{50}$ was determined from an inhibition response curve, logit-log plot of %B/B$_O$ vs concentration of test compound.

Ki was calculated by the Cheng and Prustoff transformation:

$$Ki=IC_{50}/(1+[L]/K_D)$$

where [L] is the concentration of $^3$H-ketanserin used in the assay and K$_D$ is the dissociation constant of $^3$H-ketanserin determined independently under the same binding conditions.

EXAMPLE 6

Dopamine Receptor Binding Assay

D2 and D4 receptor-binding affinities of the compounds of examples 1 and 2 were evaluated according to their ability to reduce binding of $^3$H-spiperone as compared to the reference compound clozapine. The potency of the test compound to reduce $^3$H-spiperone binding directly correlated to its binding affinity for the receptor.

D4 Receptor Preparation

HEK 298 (human embryonic kidney) cells stably transfected with human D4 receptor (D4.2 sub-type) were grown in NUNC cell factories for 5 days (75% confluency) without a media change and removed with versene (approximately 19 mg of cells per cell factory tray). The cells were then centrifuged in a Sorval centrifuge for 10 minutes, 5000 rpm (GS3 rotor) and the pellets quickly frozen in liquid nitrogen and stored at −80° C. until used in binding assay. When used in the assay, cells were thawed on ice for 20 minutes and then 10 mL of incubation buffer (50 mM Tris, 1 mM EDTA, 4 mM $MgCl_2$, 5 mM KCl, 1.5 mM $CaCl_2$, 120 mM NaCl, pH7.4) was added. The cells were then vortexed to resuspend pellet and homogenized with a Kinematica CH-6010 Kriens-LU homogenizer for 15 seconds at setting 7. Concentration of receptor protein was determined using the Pierce BCA assay.

D2 Receptor Preparation $GH_4C_1$ (rat pituitary) cells stably transfected with the human D2 receptor (short isoform) were grown in $CO_2$ independent media in roller bottles (1500 $cm^2$) for 10 days. 100 $\mu$M $ZnSO_4$ was added to the cells (the D2 promoter being zinc inducible). After 16 hours, fresh media was added to allow the cells to recover for 24 hours. The cells were harvested using versene and then centrifuged in a Sorval centrifuge for 10 minutes, at 5000 rpm (GS3 rotor). Pellets were quickly frozen in liquid nitrogen and stored at −80° C. until used in the binding assays. When used in the assay, cells were thawed on ice for 20 minutes. Each roller bottle produced approximately 72 mg of protein. 10 mL of incubation buffer was added to the pellets which were then vortexed, resuspended and homogenized with a Kinematica CH-6010 Kriens-LU homogenizer for 15 seconds at setting 7. The receptor protein concentration was determined using the Pierce BCA assay.

Total Spiperone Binding Assay

The incubation was started by the addition of 500 $\mu$l (50 $\mu$g protein) membrane homogenate to a solution of 900 $\mu$l incubation buffer and 100 $\mu$l (0.25 nM final conc.) $^3$H-spiperone (90 Ci/mmol Amersham diluted in borosilicate glass vial) in 12×75 mm polypropylene tubes. The tubes were vortexed and incubated at room temperature for 90 minutes. The binding reaction was stopped by filtering using a Brandell Cell Harvester. The samples were filtered under vacuum over glass fibre filters (Whatman GF/B) presoaked for 2 hours in 0.3% polyethylenimine (PEI) in 50 mM Tris buffer (pH7.4). The filters were then washed 3 times with 5 mL ice cold 50 mM Tris buffer (pH7.4). Individual filter disks were put in scintillation vials (Biovials, Bechman). Ready Protein Plus liquid scintillant (5 mL, Beckman) was added and the vials counted by liquid scintillation spectrophotometry (Beckman LSC 6500) after equilibrating for three hours at room temperature to determine total binding ($B_T$).

Non-Specific Binding Assay for D4

The incubation was started by the addition of 500 $\mu$l (50 $\mu$g protein) membrane homogenate to a solution of 400 $\mu$l incubation buffer, 100 $\mu$l $^3$H-spiperone (90 Ci/mmol Amersham diluted in borosilicate glass vial to 0.25 nM final conc.) and 500 $\mu$l (30 $\mu$M final conc.) of fresh dopamine (Research Biochemicals Inc., light protected and dissolved in incubation buffer) in 12×75 mm polypropylene tubes. The tubes were vortexed and incubated at room temperature for 90 minutes at which time the binding reaction was stopped by filtering. The filters were washed and counted using the same procedure as in the total binding assay described above to give the non-specific binding value (NSB).

Non-Specific Binding Assay for D2

This assay employed the same procedures as the non-specific binding assay for D4 with the exception that 2 $\mu$M (final conc.) of (−) sulpiride (Research Chemicals Inc.) was used in place of dopamine.

Displacement Binding Assay

The incubation was started by the addition to 12×75 mm polypropylene tubes 500 $\mu$l (50 $\mu$g protein) membrane homogenate to a solution of 400 $\mu$l incubation buffer, 100 $\mu$l (0.25 final conc.) $^3$H-spiperone (90 Ci/mmol, Amersham, diluted in borosilicate glass vial to) and 500 $\mu$l of test compound that was prepared from 1 mM stock dissolved in DMSO and stored at −20° C. in polypropylene cryogenic storage vials until dilution in incubation buffer in borosilicate glass vials. The tubes were vortexed and incubated at room temperature for 90 minutes at which time the binding reaction was stopped by filtering. The filters were washed and counted using the same procedure as in the total binding assay described above to give the displacement binding value ($B_D$).

Calculations

The test compounds were initially assayed at 1 and 0.1 $\mu$M and then at a range of concentrations chosen such that the middle dose would cause about 50% inhibition of $^3$H-spiperone binding. Specific binding in the absence of test compound ($B_O$) was the difference of total binding ($B_T$) minus non-specific binding (NSB) and similarly specific binding (in the presence of test compound) (B) was the difference of displacement binding ($B_D$) minus non-specific binding (NSB). $IC_{50}$ was determined from an inhibition response curve, logit-log plot of %B/$B_O$ vs concentration of test compound.

Ki was calculated by the Cheng and Prustoff transformation:

$$Ki = IC_{50}/(1+[L]/K_D)$$

where [L] is the concentration of $^3$H-spiperone used in the assay and $K_D$ is the dissociation constant of $^3$H-spiperone determined independently under the same binding conditions.

Assay results are reported in the following Table:

| RECEPTOR AFFINITIES (Ki in nM) | | | | |
|---|---|---|---|---|
| COMPOUND | STRUCTURE | D4 | D2 | 5-HT2 |
| clozapine | 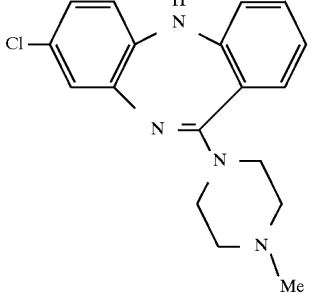 | 23 | 230 | 7.5 |
| 8-chloro-11-(3,5-dimethyl-1-piperazinyl)-dibenz[b,f][1,4]oxazepine | 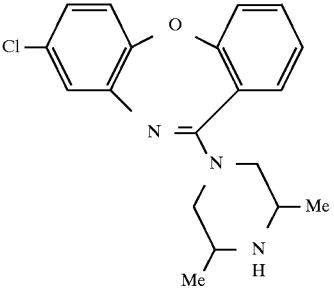 | 215 | 2169 | 13.4 |
| 11-(3,5-dimethyl-1-piperazinyl)-dibenz[b,f][1,4]oxazepine | 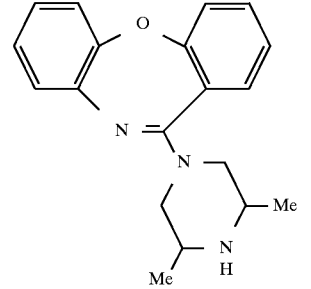 | 1097 | 6326 | 368 |
| 3-chloro-11-(3,5-dimethyl-1-piperazinyl)-5H-dibenz[b,e][1,4]diazepine | 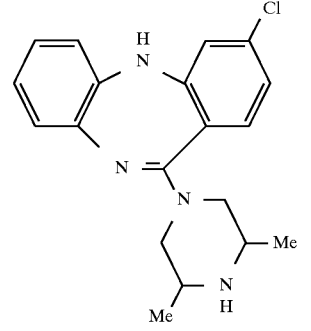 | 2753 | 14083 | 24 |
| 11-(2,5-dimethyl-1-piperazinyl)-dibenz[b,f][1,4]oxazepine | 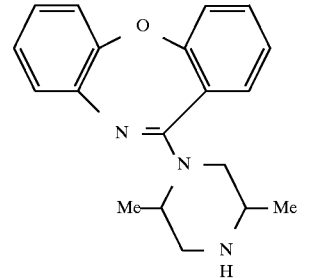 | 4538 | 4893 | 92 |

We claim:
1. A compound of Formula 1:

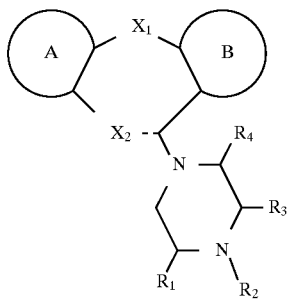

wherein
A and B are benzene unsubstituted or substituted with substituents selected independently from hydroxyl, halo, $C_{1-4}$ alkyl, amino, nitro, cyano, halo-substituted $C_{1-4}$alkyl, $C_{1-4}$alkoxy, halo-substituted $C_{1-4}$ alkoxy, $C_{1-4}$alkoxycarbonyl, $C_{1-4}$CO—, cyclo-$C_{3-7}$alkyl, HS—$C_{1-4}$alkylene, $C_{1-4}$alkylthio, halo-substituted $C_{1-4}$alkylthio, cyanothio, tetrazolyl, N-piperidinyl, N-piperazinyl, N-morpholinyl, acetamido, $C_{1-4}$alkylsulfonyl, halosulfonyl, halo-substituted $C_{1-4}$ alkylsulfonyl, $C_{1-4}$alkylsulfoxyl $SO_2NH_2$, $C_{1-4}$ alkylseleno, and $OSO_3H$;
$X_1$ is selected from O, and S;
$X_2$—is N=;
$R_1$ is $C_{1-6}$alkyl unsubstituted or substituted with a substituent selected from OH, halo, $C_{1-4}$alkyl and $C_{1-4}$alkoxy; and
$R_2$, $R_3$ and $R_4$ are independently selected from H and $R_1$; and acid addition salts, solvates and hydrates thereof.

2. The compound according to claim 1, wherein A and B are both benzene unsubstituted or substituted with 1 or 2 substituents selected independently from hydroxyl, halo, $C_{1-4}$alkyl, amino, nitro, cyano, halo-substituted $C_{1-4}$alkyl, $C_{1-4}$alkoxy, halo-substituted $C_{1-4}$ alkoxy, $C_{1-4}$alkoxycarbonyl, $C_{1-4}$CO—, cyclo-$C_{3-7}$alkyl, HS—$C_{1-4}$alkylene, $C_{1-4}$ alkylthio, halo-substituted $C_{1-4}$alkylthio, cyanothio, tetrazolyl, N-piperidinyl, N-piperazinyl, N-morpholinyl, acetamido, $C_{1-4}$alkylsulfonyl, halosulfonyl, halo-substituted $C_{1-4}$ alkylsulfonyl, $C_{1-4}$alkylsulfoxyl, $SO_2NH_2$, $C_{1-4}$alkylseleno, and $OSO_3H$.

3. The compound according to claim 1, wherein A is benzene optionally substituted by 1 or 2 chloro substituents.

4. The compound according to claim 1 wherein B is benzene optionally substituted by 1 or 2 chloro substituents.

5. The compound according to claim 1, wherein $X_1$ and $X_2$—with rings A and B form the tricycle dibenzo[b,f][1,4]oxazepine that is optionally 8-chloro-substituted.

6. The compound according to claim 1, wherein $R_1$ is $C_{1-6}$alkyl and $R_2$, $R_3$ and $R_4$ are selected from H and $C_{1-6}$alkyl.

7. The compound according to claim 6, wherein $R_1$ and $R_3$ are $C_{1-6}$alkyl and $R_2$ and $R_4$ are H.

8. The compound according to claim 7, wherein $R_1$ and $R_3$ are methyl.

9. The compound according to claim 2, wherein $R_1$ and $R_3$ are methyl and $R_2$ and $R_4$ are H.

10. The compound according to claim 1, wherein said compound is selected from 8-chloro-11-(3,5-dimethyl-1-piperazinyl)-dibenz[b,f][1,4]oxazepine;

11-(3,5-dimethyl-1-piperazinyl)dibenz[b,f][1,4]oxazepine; and 11-(2,5-dimethyl-1-piperazinyl)-dibenz[b,f][1,4]oxazepine.

11. The compound according to claim 10, wherein said compound is 8-chloro-11-(3,5-dimethyl-1-piperazinyl)-dibenz[b,f][1,4]oxazepine.

12. The compound according to claim 10, wherein said compound is 11-(2,5-dimethyl-1-piperazinyl)-dibenz[b,f][1,4]oxazepine.

13. A pharmaceutical composition, comprising a compound according to claim 1, and a pharmaceutically acceptable carrier.

14. A pharmaceutical composition, comprising a compound according to claim 10, and a pharmaceutically acceptable carrier.

15. A pharmaceutical composition, comprising a compound according to claim 11, and a pharmaceutically acceptable carrier.

16. A pharmaceutical composition, comprising a compound according to claim 12, and a pharmaceutically acceptable carrier.

17. A pharmaceutical composition, comprising an amount of the compound according to claim 1 effective to treat schizophrenia, and a pharmaceutically acceptable carrier.

* * * * *